US012280130B2

(12) United States Patent
Budde et al.

(10) Patent No.: US 12,280,130 B2
(45) Date of Patent: Apr. 22, 2025

(54) FUNCTIONALIZED CALCIUM CARBONATE FOR SUN PROTECTION BOOSTING

(71) Applicant: Omya International AG, Oftringen (CH)

(72) Inventors: Tanja Budde, Brittnau (CH); Anaïs Hecker, Lyss (CH)

(73) Assignee: Omya International AG, Oftringen (CH)

( * ) Notice: Subject to any disclaimer, the term of this patent is extended or adjusted under 35 U.S.C. 154(b) by 94 days.

(21) Appl. No.: 16/483,909

(22) PCT Filed: Feb. 2, 2018

(86) PCT No.: PCT/EP2018/052616
§ 371 (c)(1),
(2) Date: Aug. 6, 2019

(87) PCT Pub. No.: WO2018/146006
PCT Pub. Date: Aug. 16, 2018

(65) Prior Publication Data
US 2019/0380927 A1    Dec. 19, 2019

Related U.S. Application Data

(60) Provisional application No. 62/459,667, filed on Feb. 16, 2017.

(30) Foreign Application Priority Data

Feb. 9, 2017  (EP) ................................. 171554256

(51) Int. Cl.
| | |
|---|---|
| *A61K 8/19* | (2006.01) |
| *A61K 8/02* | (2006.01) |
| *A61K 8/27* | (2006.01) |
| *A61K 8/29* | (2006.01) |
| *A61Q 17/04* | (2006.01) |

(52) U.S. Cl.
CPC .............. *A61K 8/19* (2013.01); *A61K 8/0279* (2013.01); *A61K 8/27* (2013.01); *A61K 8/29* (2013.01); *A61Q 17/04* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 5,275,806 | A | 1/1994 | Gbogi et al. |
| 2003/0213937 | A1 | 11/2003 | Yaniv |

FOREIGN PATENT DOCUMENTS

| | | | |
|---|---|---|---|
| EP | 1955691 | A1 | 8/2008 |
| EP | 2168572 | A1 | 3/2010 |
| EP | 2910237 | A1 | 8/2015 |
| JP | H09132514 | A | 5/1997 |
| JP | H1160220 | A | 3/1999 |
| JP | 2011236182 | A | 11/2011 |
| JP | 2012504577 | A | 2/2012 |
| JP | 2012240930 | A | 12/2012 |
| JP | 2013510862 | A | 3/2013 |
| WO | WO-0039222 | A1 | 7/2000 |
| WO | WO-2010037753 | A1 | 4/2010 |
| WO | WO-2011060099 | A3 | 11/2011 |
| WO | WO-2015181306 | A1 | 12/2015 |
| WO | WO-2018146006 | A1 | 8/2018 |

OTHER PUBLICATIONS

"International Application Serial No. PCT/EP2018/052616, International Search Report mailed Mar. 29, 2018", 5 pgs.
"International Application Serial No. PCT/EP2018/052616, Written Opinion mailed Mar. 29, 2018", 7 pgs.

*Primary Examiner* — David J Blanchard
*Assistant Examiner* — Sarah J Chickos
(74) *Attorney, Agent, or Firm* — Schwegman Lundberg & Woessner, P.A.

(57) ABSTRACT

The present invention relates to a cosmetic composition having UV-A and/or UV-B protection comprising at least one inorganic UV filter, and surface-reacted calcium carbonate having a volume median particle size $d_{50}$ from 0.1 to 90 μm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

12 Claims, No Drawings

FUNCTIONALIZED CALCIUM CARBONATE FOR SUN PROTECTION BOOSTING

CROSS-REFERENCE TO RELATED APPLICATION

This application is a U.S. National Stage Filing under 35 U.S.C. 371 from International Application No. PCT/EP2018/052616, filed on Feb. 2, 2018, and published as WO 2018/146006 on Aug. 16, 2018, which application claims the benefit of U.S. Provisional Application Ser. No. 62/459,667, filed Feb. 16, 2017, and also claims the benefit of European Application No. 17155425.6, filed Feb. 9, 2017, all of which are incorporated herein by reference in their entirety.

The present invention relates to the field of sunscreen compositions, and in particular to a cosmetic composition having UV-A and/or UV-B protection, a method of producing the same, and the use of surface-reacted calcium carbonate for boosting the sun protection factor and/or the sensory properties of cosmetic compositions.

It is well known that the ultraviolet portion of the sun's spectrum has a damaging effect on the human skin. In particular, the ultraviolet B (UV-B) radiation ranges from 290 to 315 nm and is considered as directly damaging the DNA and causes sunburn. In contrast thereto, the ultraviolet A (UV-A) radiation ranges from 315 to 400 nm and was considered as being less damaging to the skin than the UV-B radiation for a long time. However, it is meanwhile known that the UV-A radiation causes actually more damages to the skin than UV-B radiation. Such damage is typically generated by the formation of free radicals and other reactive species developed through phototoxic reactions in the epidermis and dermis of the skin. As a consequence, the UV-A radiation is now considered as a main factor in the development of chronic light-induced alterations such as premature ageing of the skin, and thus, in the development of skin cancer. Therefore, it is becoming increasingly important to protect at least the part of the skin which is exposed to sun light against UV-B as well as UV-A radiation.

In order to achieve a broad spectrum of UV protection, sunscreen formulation typically comprise a combination of several organic UV filters, which may be supplemented with inorganic UV filters in order to increase the efficiency.

However, the use of organic UV filters such as octocrylene is subject to continuously increasing concerns especially because they are suspected to be a possible cause of skin irritations and allergies in sensitive persons and their potentially harmful effect on the environment. It is assumed that on absorbing the UV photons, organic UV filters can release free radicals and consequently cause damage to collagen, elastin or skin cell DNA (cf. Manaia et al., BJPS, 2013, 49(2), 201-209).

In contrast, inorganic UV filters are photostable and give a broader spectrum protection covering UV-A and UV-B. It is also known that inorganic UV filters cause less skin irritation. Therefore, so-called mineral-only sunscreen formulations, i.e. sunscreen formulations comprising solely inorganic UV filter materials, gain more popularity, and are especially recommended for people with sensitive skin as well as for babies and toddlers. Moreover, organic cosmetics and therefore also organic sunscreen formulations have become a major trend in recent years, which do not allow the use of synthetic ingredients.

One of the main disadvantages of inorganic UV filters, however, is that they may lead to a "whitening" effect on the skin, which is not very appealing from an aesthetical point of view. Another problem with inorganic UV filters is that in order to provide an effective light shielding ability in the ultraviolet light region while maintaining high transparency in the visible light region, inorganic UV filters are typically employed in form of nanoscale pigments. Such nanoscale particles, however, tend to agglomerate, which may reduce the sunscreen efficiency and may lead to a patchy tan. Moreover, particle agglomeration may reduce the spreadability of the formulation and may result in unpleasant sensory characteristics of the formulation.

U.S. Pat. No. 5,902,569 A discloses ultraviolet shielding composite fine particles having transparency in a visible light region comprising matrix particles and daughter particles, wherein the daughter particles are dispersed in and supported by said matrix particles, wherein the daughter particles have a smaller band gap energy than the particles constituting the matrix particles and are capable of absorbing ultraviolet light, and the resulting ultraviolet shielding composite fine particles have substantially no catalytic activity.

US 2008/0075746 A1 describes a method for the enhancement of light protection of a cosmetic or dermatological composition, said method comprising adding an insoluble or sparingly soluble micronized substance to said composition, and dispersing said micronized substance in the oil or water phase of said composition, wherein said composition further comprises at least one cosmetic UV filter that is soluble in the water or oil phase and with the proviso that said micronized substance is not a cosmetic UV absorber.

An SPF-boosting composition comprising a non-volatile oil, an aqueous phase, and about an SPF-inflection concentration of a cosmetic powder is disclosed in US 2011/0250250 A1.

WO 2016/020287 relates to a cosmetic formulation having UV-A and/or UV-B protection without organic UV-filters, wherein the cosmetic formulation comprises a base formulation comprising a water-based and an oil-based dispersion comprising at least one titanium dioxide-containing material.

Thus, there is still a need in the art for cosmetic formulations providing sufficient UV-A and/or UV-B protection.

Accordingly, it is an object of the present invention to prove a cosmetic composition having UV-A and/or UV-B protection. It is desirable that the cosmetic composition does not require the presence of organic UV filters having a potentially harmful effect on the environment or a skin irritating or allergenic potential for human beings.

It is also an object of the present invention to provide a cosmetic composition having UV-A and/or UV-B protection with improved sunscreen efficiency. For example, it would be desirable that the cosmetic composition provides an improved UV filter performance, and thus, may allow to reduce the amount of UV filter agent without affecting the envisaged sun protection factor (SPF).

It is also an object of the present invention to provide a cosmetic composition having UV-A and/or UV-B protection with improved appearance and/or sensory properties. It would be desirable that the cosmetic composition shows a reduced whitening effect when applied to the skin. Furthermore, it would be desirable that the cosmetic composition can be easily applied to the skin and forms an even and uniform film on the skin. Moreover, it would be desirable that the cosmetic composition is less greasy and sticky. It would also be desirable that the cosmetic composition exhibits a good spreadability and dries fast.

Furthermore, it is an object of the present invention to provide a cosmetic composition having UV-A and/or UV-B protection, which is derivable from natural sources. It is also desirable to provide a cosmetic composition which is easily biodegradable.

The foregoing and other objects are solved by the subject-matter as defined in the independent claims.

According to one aspect of the present invention, a cosmetic composition having UV-A and/or UV-B protection is provided, comprising
- at least one inorganic UV filter, and
- surface-reacted calcium carbonate having a volume median particle size $d_{50}$ from 0.1 to 90 µm,
  wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

According to another aspect of the present invention a method for producing a cosmetic composition is provided, wherein at least one inorganic UV filter is mixed with surface-reacted calcium carbonate having a volume median particle size $d_{50}$ from 0.1 to 90 µm,
  wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

According to still another aspect of the present invention, use of surface-reacted calcium carbonate for boosting the sun protection factor (SPF) of a cosmetic composition having UV-A and/or UV-B protection and comprising at least one inorganic UV filter is provided,
  wherein the surface-reacted calcium carbonate has a volume median particle size $d_{50}$ from 0.1 to 90 µm, and
  the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

According to still another aspect of the present invention, use of surface-reacted calcium carbonate for improving the sensory properties of a cosmetic composition having UV-A and/or UV-B protection and comprising at least one inorganic UV filter is provided,
  wherein the surface-reacted calcium carbonate has a volume median particle size $d_{50}$ from 0.1 to 90 µm, and
  the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

Advantageous embodiments of the present invention are defined in the corresponding subclaims.

According to one embodiment the at least one inorganic UV filter is selected from the group consisting of titanium dioxide, zinc oxide, iron oxide, hydroxyapatite, cerium oxide, calcium-doped cerium oxide, cerium phosphate, and mixtures thereof, preferably the least one inorganic UV filter is selected from the group consisting of titanium dioxide, zinc oxide, hydroxyapatite, and mixtures thereof, more preferably the at least one inorganic UV filter is titanium dioxide and/or zinc oxide, and most preferably the at least one inorganic UV filter is titanium dioxide. According to another embodiment the at least one inorganic UV filter is in form of particles having a weight median particle size $d_{50}$ from 10 to 1 000 nm, preferably from 12 to 800 nm, more preferably from 15 to 600 nm, and most preferably from 20 to 400 nm. According to still another embodiment the at least one inorganic UV filter is present in an amount from 1 to 50 wt.-%, based on the total weight of the cosmetic composition, preferably from 2 to 40 wt.-%, more preferably from 5 to 30 wt.-%, and most preferably from 10 to 25 wt.-%.

According to one embodiment the surface-reacted calcium carbonate has a volume median particle size $d_{50}$ from 0.1 to 75 µm, preferably from 0.5 to 50 µm, more preferably from 1 to 40 µm, even more preferably from 1.2 to 30 µm, and most preferably from 1.5 to 15 µm. According to another embodiment the surface-reacted calcium carbonate has a specific surface area of from 15 $m^2/g$ to 200 $m^2/g$, preferably from 20 $m^2/g$ to 180 $m^2/g$, more preferably from 25 $m^2/g$ to 160 $m^2/g$, even more preferably from 27 $m^2/g$ to 150 $m^2/g$, and most preferably from 30 $m^2/g$ to 140 $m^2/g$, measured using nitrogen and the BET method.

According to one embodiment the natural ground calcium carbonate is selected from the group consisting of marble, chalk, limestone, and mixtures thereof, or the precipitated calcium carbonate is selected from the group consisting of precipitated calcium carbonates having an aragonitic, vateritic or calcitic crystal form, and mixtures thereof.

According to one embodiment the at least one $H_3O^+$ ion donor is selected from the group consisting of hydrochloric acid, sulphuric acid, sulphurous acid, phosphoric acid, citric acid, oxalic acid, an acidic salt, acetic acid, formic acid, and mixtures thereof, preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a cation selected from $Li^+$, $Na^+$ and/or $K^+$, $HPO_4^{2-}$, being at least partially neutralised by a cation selected from $Li^+$, $Na^+$, $K^+$, $Mg^{2+}$, and/or $Ca^{2+}$, and mixtures thereof, more preferably the at least one $H_3O^+$ ion donor is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid. According to another embodiment the surface-reacted calcium carbonate is present in an amount from 0.1 to 50 wt.-%, based on the total weight of the cosmetic composition, preferably from 0.5 to 20 wt.-%, more preferably from 1 to 10 wt.-%, and most preferably from 3 to 6 wt.-%.

According to one embodiment the cosmetic composition further comprises at least one organic UV filter, preferably the at least one organic UV filter is selected from the group consisting of derivatives of cinnamic acid and its salts, derivatives of salicylic acid and its salts, benzophenones, derivatives of aminobenzoic acid and its salts, dibenzoyl-methanes, benzylidenecamphor derivatives, benzimidazole derivatives, diphenylacrylate derivatives, acrylamide derivatives, benzotriazole derivatives, triazine derivatives, benzalmalonate derivatives, aminobenzoate derivatives, octocrylene, and mixtures thereof, and more preferably the at least one organic UV filter is selected from the group consisting of derivatives of cinnamic acid and its salts, benzophenones, octocrylene, and mixtures thereof. According to another embodiment the cosmetic composition further comprises at least one additive selected from the group consisting of bleaching agents, thickeners, stabilizers, chelating agents, preserving agents, wetting agents, emulsifiers, emollients, fragrances, colorants, skin tanning compounds, antioxidants, pigments, oils, water, and mixtures thereof.

According to one embodiment the cosmetic composition is a sunscreen product, an eye make-up product, a facial make-up product, a lip care product, a hair care product, a hair styling product, a nail care product, a hand care product, a skin care product, or a combination product thereof. According to another embodiment the surface-reacted calcium carbonate is associated with at least one active agent selected from pharmaceutically active agents, biologically active agents, disinfecting agents, preservatives, flavouring agents, surfactants, oils, fragrances, essential oils, and mixtures thereof.

It should be understood that for the purpose of the present invention, the following terms have the following meaning:

"Natural ground calcium carbonate" (GCC) in the meaning of the present invention is a calcium carbonate obtained from natural sources, such as limestone, marble, or chalk, and processed through a wet and/or dry treatment such as grinding, screening and/or fractionating, for example, by a cyclone or classifier.

"Precipitated calcium carbonate" (PCC) in the meaning of the present invention is a synthesised material, obtained by precipitation following reaction of carbon dioxide and lime in an aqueous, semi-dry or humid environment or by precipitation of a calcium and carbonate ion source in water. PCC may be in the vateritic, calcitic or aragonitic crystal form. PCCs are described, for example, in EP 2 447 213 A1, EP 2 524 898 A1, EP 2 371 766 A1, EP 1 712 597 A1, EP 1 712 523 A1, or WO 2013/142473 A1.

The term "surface-reacted" in the meaning of the present application shall be used to indicate that a material has been subjected to a process comprising partial dissolution of said material upon acidic treatment (e.g., by use of water-soluble free acids and/or acidic salts) in aqueous environment followed by a crystallization process which may occur in the absence or presence of further crystallization additives. The term "acid" as used herein refers to an acid in the meaning of the definition by Brønsted and Lowry (e.g., $H_2SO_4$, $HSO_4^-$), wherein the term "free acid" refers only to those acids being in the fully protonated form (e.g., $H_2SO_4$).

The "particle size" of particulate materials other than surface-reacted calcium carbonate herein is described by its distribution of particle sizes $d_x$. Therein, the value $d_x$ represents the diameter relative to which x % by weight of the particles have diameters less than $d_x$. This means that, for example, the $d_{20}$ value is the particle size at which 20 wt.-% of all particles are smaller than that particle size. The $d_{50}$ value is thus the weight median particle size, i.e. 50 wt.-% of all particles are smaller than this particle size. For the purpose of the present invention, the particle size is specified as weight median particle size $d_{50}$ (wt.) unless indicated otherwise. Particle sizes were determined by using a Sedigraph™ 5100 instrument or Sedigraph™ 5120 instrument of Micromeritics Instrument Corporation. The method and the instrument are known to the skilled person and are commonly used to determine the particle size of fillers and pigments. The measurements were carried out in an aqueous solution of 0.1 wt.-% $Na_4P_2O_7$.

The "particle size" of surface-reacted calcium carbonate herein is described as volume-based particle size distribution. Volume median particle size $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005.

The term "particulate" in the meaning of the present application refers to materials composed of a plurality of particles. Said plurality of particles may be defined, for example, by its particle size distribution. The expression "particulate material" may comprise granules, powders, grains, tablets, or crumbles.

The "specific surface area" (expressed in $m^2/g$) of a material as used throughout the present document can be determined by the Brunauer Emmett Teller (BET) method with nitrogen as adsorbing gas and by use of a ASAP 2460 instrument from Micromeritics. The method is well known to the skilled person and defined in ISO 9277:2010. Samples are conditioned at 100° C. under vacuum for a period of 30 min prior to measurement. The total surface area (in $m^2$) of said material can be obtained by multiplication of the specific surface area (in $m^2/g$) and the mass (in g) of the material.

In the context of the present invention, the term "pore" is to be understood as describing the space that is found between and/or within particles, i.e. that is formed by the particles as they pack together under nearest neighbour contact (interparticle pores), such as in a powder or a compact and/or the void space within porous particles (intraparticle pores), and that allows the passage of liquids under pressure when saturated by the liquid and/or supports absorption of surface wetting liquids.

For the purpose of the present invention, the "solids content" of a liquid composition is a measure of the amount of material remaining after all the solvent or water has been evaporated. If necessary, the "solids content" of a suspension given in wt.-% in the meaning of the present invention can be determined using a Moisture Analyzer HR73 from Mettler-Toledo (T=120° C., automatic switch off 3, standard drying) with a sample size of 5 to 20 g.

Unless specified otherwise, the term "drying" refers to a process according to which at least a portion of water is removed from a material to be dried such that a constant weight of the obtained "dried" material at 120° C. is reached. Moreover, a "dried" or "dry" material may be defined by its total moisture content which, unless specified otherwise, is less than or equal to 1.0 wt.-%, preferably less than or equal to 0.5 wt.-%, more preferably less than or equal to 0.2 wt.-%, and most preferably between 0.03 and 0.07 wt.-%, based on the total weight of the dried material.

For the purpose of the present application, "water-insoluble" materials are defined as those which, when mixed with 100 ml of deionised water and filtered at 20° C. to recover the liquid filtrate, provide less than or equal to 0.1 g of recovered solid material following evaporation at 95 to 100° C. of 100 g of said liquid filtrate. "Water-soluble" materials are defined as materials leading to the recovery of greater than 0.1 g of solid material following evaporation at 95 to 100° C. of 100 g of said liquid filtrate. In order to assess whether a material is an insoluble or soluble material in the meaning of the present invention, the sample size is greater than 0.1 g, preferably 0.5 g or more.

A "suspension" or "slurry" in the meaning of the present invention comprises undissolved solids and water, and optionally further additives, and usually contains large amounts of solids and, thus, is more viscous and can be of higher density than the liquid from which it is formed.

Where an indefinite or definite article is used when referring to a singular noun, e.g., "a", "an" or "the", this includes a plural of that noun unless anything else is specifically stated.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

The inventive cosmetic composition having UV-A and/or UV-B protection comprises at least one inorganic UV filter, and surface-reacted calcium carbonate having a volume median particle size $d_{50}$ from 0.1 to 90 μm. The surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source In the following preferred embodiments of the inventive composition will be set out in more detail. It is to be understood that these embodiments and details also apply to the inventive methods and uses.

Inorganic UV Filter

The cosmetic composition of the present invention comprises at least one inorganic UV filter.

The term "inorganic UV filter" as used herein refers to an inorganic particulate material, which can reflect, scatter and/or absorb ultraviolet (UV) radiation in the UV-A and/or UV-B region of the electromagnetic spectrum, i.e. electromagnetic radiation having a wavelength between 290 and 400 nm.

The expression "at least one" inorganic UV filter in the meaning of the present invention means that the cosmetic composition comprises one or more types of inorganic UV filter materials. For example, the cosmetic composition may comprise a mixture of two or three inorganic UV filters. According to a preferred embodiment, the cosmetic composition comprises one inorganic UV filter.

Any inorganic UV filter known in the art and suitable for cosmetic applications may be used. Examples of materials that are suitable as inorganic UV filter are titanium dioxide, zinc oxide, iron oxide, hydroxyapatite, cerium oxide, calcium-doped cerium oxide, or cerium phosphate.

According to one embodiment of the present invention, the at least one inorganic UV filter is selected from the group consisting of titanium dioxide, zinc oxide, iron oxide, hydroxyapatite, cerium oxide, calcium-doped cerium oxide, cerium phosphate, and mixtures thereof, preferably the least one inorganic UV filter is selected from the group consisting of titanium dioxide, zinc oxide, hydroxyapatite, and mixtures thereof, more preferably the at least one inorganic UV filter is titanium dioxide and/or zinc oxide, and most preferably the at least one inorganic UV filter is titanium dioxide.

The at least one inorganic UV filter may be present in form of particles. According to one embodiment the at least one inorganic UV filter is in form of particles having a weight median particle size $d_{50}$ from 10 to 1 000 nm, preferably from 12 to 800 nm, more preferably from 15 to 600 nm, and most preferably from 20 to 400 nm. The surface of said particles can be uncoated or can be at least partially coated, for example, in order to improve their dispersibility or to prevent any potential photocatalytic activity of said materials. Examples of suitable surface coating materials are silica, hydrated silica, alumina, aluminium hydroxide, aluminium stearate, stearic acid, trimethoxycaprylsilane, glycerine, dimethicone, hydrogen dimethicone, simeticone, and mixtures thereof. However, any other suitable coating material known the skilled person may be used.

According to one embodiment of the present invention, the at least one inorganic UV filter comprises zinc oxide. The surface of the zinc dioxide particles may be uncoated or may be at least partially coated. Examples of suitable surface coating materials are triethoxycaprylsilane, dimethicone, dimethoxydiphenylsilanetriethoxycaprylsilane cross-copolymer, octyl-triethoxy silane, and mixtures thereof. According to an exemplary embodiment, the surface of the zinc oxide particles is at least partially surface-coated with triethoxycaprylsilane. However, any other suitable coating material known the skilled person may be used.

According to another embodiment of the present invention, the at least one inorganic UV filter comprises titanium dioxide. According to a preferred embodiment, the at least one inorganic UV filter consists of titanium dioxide and zinc oxide, and most preferably the at least one inorganic UV filter consists of titanium dioxide.

Titanium dioxide can have an anatase, rutile, or amorphous structure. It is preferred that the titanium dioxide particles are in crystalline form. According to one embodiment, the crystallinity of titanium dioxide is in the range from 10 to 100 wt.-%, preferably from 40.0 to 100.0 wt.-%, more preferably above 60.0 wt.-%, and most preferably above 70.0 wt.-%, based on the total dry weight of the titanium dioxide. The crystallinity may be determined by X-ray diffraction.

According to one embodiment titanium dioxide is in rutile from. According to another embodiment titanium dioxide is in rutile and anatase form. Preferably, the titanium dioxide may comprise titanium dioxide mainly in rutile form, i.e. small amounts may also be in a brookite and/or anatase form. For example, the titanium dioxide may comprise at least 10 wt.-% of rutile structure, preferably at least 25 wt.-%, more preferably at least 50 wt.-% and most preferably at least 75 wt.-%, based on the total dry weight of titanium dioxide. According to one embodiment, the titanium dioxide is in rutile form comprising up to 5 wt.-%, based on the total dry weight of the titanium dioxide, of anatase. The term "dry" titanium dioxide refers to titanium dioxide particles having a total surface moisture content of less than 0.5 wt.-%, preferably less than 0.2 wt.-% and more preferably less than 0.1 wt.-%, based on the total weight of the particles.

According to one embodiment, the titanium dioxide is composed of rutile in an amount of ≥75 wt.-%, based on the total dry weight of titanium dioxide, and anatase in an amount of ≤25 wt.-%, based on the total dry weight of titanium dioxide. For example, the titanium dioxide is composed of rutile in an amount of ≥90 wt.-%, based on the total dry weight of titanium dioxide, and anatase in an amount of <10 wt.-%, based on the total dry weight of titanium dioxide. Preferably, the titanium dioxide is essentially composed of rutile, i.e. in an amount of about 100 wt.-%, based on the total dry weight of titanium dioxide.

Titanium dioxide particles are usually prepared in the chloride process, in which $TiCl_4$ is oxidized to $TiO_2$ particles, or in the sulfate process, in which sulfuric acid and ore containing titanium are dissolved, and the resulting solution goes through a series of steps to yield the at least one titanium dioxide-containing particles.

The titanium dioxide can be essentially pure titanium dioxide or may contain other metal oxides, such as silica, alumina, zirconia and the like, preferably silica. Such other metal oxides may be incorporated into the titanium dioxide particles by co-oxidizing or co-precipitating titanium compounds with other metal compounds during their preparation in the chloride or sulfate process. If other metal oxides are incorporated into the titanium dioxide, the other metal oxides are preferably present in an amount of less than 40 wt.-%, more preferably in an amount of less than 35 wt.-%, even more preferably in an amount of less than 30.0 wt.-% and most preferably in an amount of less than 25.0 wt.-%, based on the total dry weight of the titanium dioxide.

The surface of the titanium dioxide particles may be uncoated or may be at least partially coated. Examples of suitable surface coating materials are silica, hydrated silica, aluminium oxide, aluminium hydroxide, aluminium stearate, stearic acid, trimethoxycaprylsilane, glycerine, dimethicone, hydrogen dimethicone, simeticone, and mixtures thereof. According to an exemplary embodiment, the surface of the titanium dioxide particles is at least partially coated with aluminium oxide and dimethicone. However, any other suitable coating material known the skilled person may be used.

According to one embodiment of the present invention, the titanium dioxide particles are at least partially covered by a hydrophilic coating. In other words, a hydrophilic titanium dioxide is obtained by surface treating the titanium dioxide with a suitable compound such that a hydrophilic coating is formed on at least a part of the surface area of the titanium dioxide.

For the purpose of the present invention, the term "hydrophilic titanium dioxide" refers to a material that comprises from 60 to 99.9 wt.-% of titanium dioxide, based on the total dry weight of the hydrophilic titanium dioxide. Thus, it is preferred that the hydrophilic titanium dioxide comprises the hydrophilic coating in an amount of from 0.1 to 40 wt.-%, based on the total dry weight of the hydrophilic titanium dioxide.

For example, the hydrophilic titanium dioxide comprises the titanium dioxide in an amount of from 70 to 99 wt.-% and the hydrophilic coating in an amount of from 1 to 30 wt.-%, based on the total dry weight of the hydrophilic titanium dioxide. Preferably, the hydrophilic titanium dioxide comprises the titanium dioxide in an amount of from 80 to 99 wt.-% and the hydrophilic coating in an amount of from 1 to 20 wt.-%, based on the total dry weight of the hydrophilic titanium dioxide. More preferably, the hydrophilic titanium dioxide comprises the titanium dioxide in an amount of from 88 to 98 wt.-% and the hydrophilic coating in an amount of from 2 to 12 wt.-%, based on the total dry weight of the hydrophilic titanium dioxide.

In one embodiment, the hydrophilic titanium dioxide comprises titanium dioxide particles which are at least partially covered by a hydrophilic coating comprising at least one compound selected from the group comprising aluminium hydroxide, alumina, silica, glycerin, silicone compounds, silane and mixtures thereof. Preferably, the hydrophilic titanium dioxide comprises titanium dioxide particles which are at least partially covered by a hydrophilic coating comprising aluminium hydroxide or glycerin. More preferably, the hydrophilic titanium dioxide comprises titanium dioxide particles which are at least partially covered by a hydrophilic coating comprising glycerin.

Examples of advantageous silicone compounds and silanes are compounds as described in, for example, EP 1 544 256 A2.

According to another embodiment of the present invention, the titanium dioxide particles are at least partially covered by a hydrophobic coating. In other words, a hydrophobic titanium dioxide is obtained by surface treating the titanium dioxide particles with a suitable compound such that a hydrophobic coating is formed on at least a part of the surface area of the titanium dioxide particles.

For the purpose of the present invention, the term "hydrophobic titanium dioxide" refers to a material that comprises from 60 to 99.9 wt.-% of titanium dioxide, based on the total dry weight of the hydrophobic titanium dioxide. Thus, it is preferred that the hydrophobic titanium dioxide comprises the hydrophobic coating in an amount of from 0.1 to 40 wt.-%, based on the total dry weight of the hydrophobic titanium dioxide.

For example, the hydrophobic titanium dioxide-containing material comprises the titanium dioxide in an amount of from 70 to 99 wt.-% and the hydrophobic coating in an amount of from 1 to 30 wt.-%, based on the total dry weight of the hydrophobic titanium dioxide. Preferably, the hydrophobic titanium dioxide comprises the titanium dioxide in an amount of from 80 to 99 wt.-% and the hydrophobic coating in an amount of from 1 to 20 wt.-%, based on the total dry weight of the hydrophobic titanium dioxide. More preferably, the hydrophobic titanium dioxide comprises the titanium dioxide in an amount of from 90 to 99 wt.-% and the hydrophobic coating in an amount of from 1 to 10 wt.-%, based on the total dry weight of the hydrophobic titanium dioxide.

In one embodiment, the hydrophobic titanium dioxide comprises titanium dioxide particles which are at least partially covered by a hydrophobic coating comprising at least one compound selected from the group comprising trimethoxy caprylsilane, triethoxy caprylsilane, dimethicone, simethicone, methicone, cyclic methicone, branched methicone, stearic acid and mixtures thereof. Preferably, the hydrophobic titanium dioxide comprises titanium dioxide particles which are at least partially covered by a hydrophobic coating comprising triethoxy caprylsilane or stearic acid. More preferably, the hydrophobic titanium dioxide comprises titanium dioxide particles which are at least partially covered by a hydrophobic coating comprising triethoxy caprylsilane.

According to another embodiment of the present invention, the titanium dioxide particles are at least partially covered by a coating comprising a mixture of hydrophilic and hydrophobic compounds. Suitable hydrophilic and hydrophobic materials are defined above.

According to one embodiment of the present invention, the at least one inorganic UV filter comprises, preferably consists of, zinc oxide and titanium dioxide, wherein the surface of the zinc oxide is at least partially coated with triethoxycaprylsilane and the surface of the titanium dioxide is at least partially coated with aluminum oxide and dimethicone.

Surface-Reacted Calcium Carbonate

In addition to the at least one inorganic UV filter, the cosmetic composition of the present invention comprises surface-reacted calcium carbonate, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donor treatment and/or is supplied from an external source.

An $H_3O^+$ ion donor in the context of the present invention is a Brønsted acid and/or an acid salt, i.e. a salt containing an acidic hydrogen.

In a preferred embodiment of the invention the surface-reacted calcium carbonate is obtained by a process comprising the steps of: (a) providing a suspension of natural or precipitated calcium carbonate, (b) adding at least one acid having a $pK_a$ value of 0 or less at 20° C. or having a $pK_a$ value from 0 to 2.5 at 20° C. to the suspension of step a), and (c) treating the suspension of step (a) with carbon dioxide before, during or after step (b). According to another embodiment the surface-reacted calcium carbonate is obtained by a process comprising the steps of: (A) providing a natural or precipitated calcium carbonate, (B) providing at least one water-soluble acid, (C) providing gaseous $CO_2$, (D) contacting said natural or precipitated calcium carbonate of step (A) with the at least one acid of step (B) and with the $CO_2$ of step (C), characterised in that: (i) the at least one acid of step B) has a $pK_a$ of greater than 2.5 and less than or equal to 7 at 20° C., associated with the ionisation of its first available hydrogen, and a corresponding anion is formed on loss of this first available hydrogen capable of forming a water-soluble calcium salt, and (ii) following contacting the at least one acid with natural or precipitated calcium carbonate, at least one water-soluble salt, which in the case of a hydrogen-containing salt has a $pK_a$ of greater than 7 at 20° C., associated with the ionisation of the first available hydrogen, and the salt anion of which is capable of forming water-insoluble calcium salts, is additionally provided.

"Natural ground calcium carbonate" (GCC) preferably is selected from calcium carbonate containing minerals selected from the group comprising marble, chalk, limestone and mixtures thereof. Natural ground calcium carbonate may comprise further naturally occurring components such as magnesium carbonate, alumino silicate etc.

In general, the grinding of natural ground calcium carbonate may be a dry or wet grinding step and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate containing mineral material comprises a wet ground calcium carbonate containing mineral material, the grinding step may be performed under conditions such that autogenous grinding takes place and/or by horizontal ball milling, and/or other such processes known to the skilled man. The wet processed ground calcium carbonate containing mineral material thus obtained may be washed and dewatered by well-known processes, e.g. by flocculation, filtration or forced evaporation prior to drying. The subsequent step of drying (if necessary) may be carried out in a single step such as spray drying, or in at least two steps. It is also common that such a mineral material undergoes a beneficiation step (such as a flotation, bleaching or magnetic separation step) to remove impurities.

"Precipitated calcium carbonate" (PCC) in the meaning of the present invention is a synthesized material, generally obtained by precipitation following reaction of carbon dioxide and calcium hydroxide in an aqueous environment or by precipitation of calcium and carbonate ions, for example $CaCl_2$) and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the precipitated calcium carbonate is precipitated calcium carbonate, preferably comprising aragonitic, vateritic or calcitic mineralogical crystal forms or mixtures thereof.

Precipitated calcium carbonate may be ground prior to the treatment with carbon dioxide and at least one $H_3O^+$ ion donor by the same means as used for grinding natural calcium carbonate as described above.

According to one embodiment of the present invention, the natural ground calcium carbonate or precipitated calcium carbonate is in form of particles having a weight median particle size $d_{50}$ of 0.05 to 10.0 μm, preferably 0.2 to 5.0 μm, more preferably 0.4 to 3.0 μm, most preferably 0.5 to 1.2 μm, especially 0.6 μm. According to a further embodiment of the present invention, the natural ground calcium carbonate or precipitated calcium carbonate is in form of particles having a weight top cut particle size $d_{98}$ of 0.15 to 30 μm, preferably 0.6 to 15 μm, more preferably 1.2 to 10 μm, most preferably 1.5 to 4 μm, especially 1.6 μm.

The natural ground calcium carbonate and/or precipitated calcium carbonate may be used dry or suspended in water. Preferably, a corresponding slurry has a content of natural ground calcium carbonate or precipitated calcium carbonate within the range of 1 wt.-% to 90 wt.-%, more preferably 3 wt.-% to 60 wt.-%, even more preferably 5 wt.-% to 40 wt.-%, and most preferably 10 wt.-% to 25 wt.-% based on the weight of the slurry.

The one or more $H_3O^+$ ion donor used for the preparation of surface-reacted calcium carbonate may be any strong acid, medium-strong acid, or weak acid, or mixtures thereof, generating $H_3O^+$ ions under the preparation conditions. According to the present invention, the at least one $H_3O^+$ ion donor can also be an acid salt, generating $H_3O^+$ ions under the preparation conditions.

According to one embodiment, the at least one $H_3O^+$ ion donor is a strong acid having a $pK_a$ of 0 or less at 20° C.

According to another embodiment, the at least one $H_3O^+$ ion donor is a medium-strong acid having a $pK_a$ value from 0 to 2.5 at 20° C. If the $pK_a$ at 20° C. is 0 or less, the acid is preferably selected from sulphuric acid, hydrochloric acid, or mixtures thereof. If the $pK_a$ at 20° C. is from 0 to 2.5, the $H_3O^+$ ion donor is preferably selected from $H_2SO_3$, $H_3PO_4$, oxalic acid, or mixtures thereof. The at least one $H_3O^+$ ion donor can also be an acid salt, for example, $HSO_4^-$ or $H_2PO_4^-$, being at least partially neutralized by a corresponding cation such as $Li^+$, $Na^+$ or $K^+$, or $HPO_4^{2-}$, being at least partially neutralised by a corresponding cation such as $Li^+$, $Na^+$, $K^+$, $Mg^{2+}$ or $Ca^{2+}$. The at least one $H_3O^+$ ion donor can also be a mixture of one or more acids and one or more acid salts.

According to still another embodiment, the at least one $H_3O^+$ ion donor is a weak acid having a $pK_a$ value of greater than 2.5 and less than or equal to 7, when measured at 20° C., associated with the ionisation of the first available hydrogen, and having a corresponding anion, which is capable of forming water-soluble calcium salts. Subsequently, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally provided. According to the preferred embodiment, the weak acid has a $pK_a$ value from greater than 2.5 to 5 at 20° C., and more preferably the weak acid is selected from the group consisting of acetic acid, formic acid, propanoic acid, and mixtures thereof. Exemplary cations of said water-soluble salt are selected from the group consisting of potassium, sodium, lithium and mixtures thereof. In a more preferred embodiment, said cation is sodium or potassium. Exemplary anions of said water-soluble salt are selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of drop wise addition, this addition preferably takes place within a time period of 10 minutes. It is more preferred to add said salt in one step.

According to one embodiment of the present invention, the at least one $H_3O^+$ ion donor is selected from the group consisting of hydrochloric acid, sulphuric acid, sulphurous acid, phosphoric acid, citric acid, oxalic acid, acetic acid, formic acid, and mixtures thereof. Preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a corresponding cation such as $Li^+$, $Na^+$ or $K^+$, $HPO_4^{2-}$, being at least partially neutralised by a corresponding cation such as $Li^+$, $Na^+$, $K^+$, $Mg^{2+}$, or $Ca^{2+}$ and mixtures thereof, more preferably the at least one acid is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

The one or more $H_3O^+$ ion donor can be added to the suspension as a concentrated solution or a more diluted solution. Preferably, the molar ratio of the $H_3O^+$ ion donor to the natural or precipitated calcium carbonate is from 0.01 to 4, more preferably from 0.02 to 2, even more preferably 0.05 to 1 and most preferably 0.1 to 0.58.

As an alternative, it is also possible to add the $H_3O^+$ ion donor to the water before the natural or precipitated calcium carbonate is suspended.

In a next step, the natural ground calcium carbonate or precipitated calcium carbonate is treated with carbon dioxide. If a strong acid such as sulphuric acid or hydrochloric acid is used for the $H_3O^+$ ion donor treatment of the natural ground calcium carbonate or precipitated calcium carbonate, the carbon dioxide is automatically formed. Alternatively or additionally, the carbon dioxide can be supplied from an external source.

$H_3O^+$ ion donor treatment and treatment with carbon dioxide can be carried out simultaneously which is the case when a strong or medium-strong acid is used. It is also possible to carry out $H_3O^+$ ion donor treatment first, e.g. with a medium strong acid having a $pK_a$ in the range of 0 to 2.5 at 20° C., wherein carbon dioxide is formed in situ, and thus, the carbon dioxide treatment will automatically be carried out simultaneously with the $H_3O^+$ ion donor treatment, followed by the additional treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably 1:0.05 to 1:5.

In a preferred embodiment, the $H_3O^+$ ion donor treatment step and/or the carbon dioxide treatment step are repeated at least once, more preferably several times. According to one embodiment, the at least one $H_3O^+$ ion donor is added over a time period of at least about 5 min, preferably at least about 10 min, typically from about 10 to about 20 min, more preferably about 30 min, even more preferably about 45 min, and sometimes about 1 h or more.

Subsequent to the $H_3O^+$ ion donor treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or precipitated calcium carbonate as an aqueous suspension having a pH of greater than 6.0, preferably greater than 6.5, more preferably greater than 7.0, even more preferably greater than 7.5.

Further details about the preparation of the surface-reacted natural calcium carbonate are disclosed in WO 00/39222 A1, WO 2004/083316 A1, WO 2005/121257 A2, WO 2009/074492 A1, EP 2 264 108 A1, EP 2 264 109 A1 and US 2004/0020410 A1, the content of these references herewith being included in the present application.

Similarly, surface-reacted precipitated calcium carbonate is obtained. As can be taken in detail from WO 2009/074492 A1, surface-reacted precipitated calcium carbonate is obtained by contacting precipitated calcium carbonate with $H_3O^+$ ions and with anions being solubilized in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilized calcium ions.

In a further preferred embodiment of the preparation of the surface-reacted natural ground calcium carbonate or precipitated calcium carbonate, the natural ground calcium carbonate or precipitated calcium carbonate is reacted with the acid and/or the carbon dioxide in the presence of at least one compound selected from the group consisting of silicate, silica, aluminium hydroxide, earth alkali aluminate such as sodium or potassium aluminate, magnesium oxide, or mixtures thereof. Preferably, the at least one silicate is selected from an aluminium silicate, a calcium silicate, or an earth alkali metal silicate. These components can be added to an aqueous suspension comprising the natural ground calcium carbonate or precipitated calcium carbonate before adding the acid and/or carbon dioxide.

Alternatively, the silicate and/or silica and/or aluminium hydroxide and/or earth alkali aluminate and/or magnesium oxide component(s) can be added to the aqueous suspension of natural or precipitated calcium carbonate while the reaction of natural or precipitated calcium carbonate with an acid and carbon dioxide has already started. Further details about the preparation of the surface-reacted natural or precipitated calcium carbonate in the presence of at least one silicate and/or silica and/or aluminium hydroxide and/or earth alkali aluminate component(s) are disclosed in WO 2004/083316 A1, the content of this reference herewith being included in the present application.

The surface-reacted calcium carbonate can be kept in suspension, optionally further stabilised by a dispersant. Conventional dispersants known to the skilled person can be used. A preferred dispersant is comprised of polyacrylic acids and/or carboxymethylcelluloses.

Alternatively, the aqueous suspension described above can be dried, thereby obtaining the solid (i.e. dry or containing as little water that it is not in a fluid form) surface-reacted natural ground calcium carbonate or precipitated calcium carbonate in the form of granules or a powder.

The surface-reacted calcium carbonate may have different particle shapes, such as e.g. the shape of roses, golf balls and/or brains.

According to one embodiment the surface-reacted calcium carbonate has a specific surface area of from 15 $m^2/g$ to 200 $m^2/g$, preferably from 20 $m^2/g$ to 180 $m^2/g$, more preferably from 25 $m^2/g$ to 160 $m^2/g$, even more preferably from 27 $m^2/g$ to 150 $m^2/g$, most preferably from 30 $m^2/g$ to 140 $m^2/g$, measured using nitrogen and the BET method. The BET specific surface area in the meaning of the present invention is defined as the surface area of the particles divided by the mass of the particles. As used therein the specific surface area is measured by adsorption using the BET isotherm (ISO 9277:1995) and is specified in $m^2/g$.

It is a requirement of the present invention that the surface-reacted calcium carbonate has a volume median particle size $d_{50}$ from 0.1 to 90 µm. According to one embodiment the surface-reacted calcium carbonate has a volume median particle size $d_{50}$ from 0.1 to 75 µm, preferably from 0.5 to 50 µm, more preferably from 1 to 40 µm, even more preferably from 1.2 to 30 µm, and most preferably from 1.5 to 15 µm.

It may furthermore be preferred that the surface-reacted calcium carbonate particles have a volume top cut particle size $d_{98}$ of from 2 to 150 µm, preferably from 4 to 100 µm, more preferably 6 to 80 µm, even more preferably from 8 to 60 µm, and most preferably from 10 to 30 µm.

The value $d_x$ represents the diameter relative to which x % of the particles have diameters less than $d_x$. This means that the $d_{98}$ value is the particle size at which 98% of all particles are smaller. The $d_{98}$ value is also designated as "top cut". The $d_x$ values may be given in volume or weight percent. The $d_{50}$ (wt) value is thus the weight median particle size, i.e. 50 wt.-% of all grains are smaller than this particle size, and the $d_{50}$ (vol) value is the volume median particle size, i.e. 50 vol. % of all grains are smaller than this particle size.

Volume median grain diameter $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005.

The weight median grain diameter is determined by the sedimentation method, which is an analysis of sedimentation behaviour in a gravimetric field. The measurement is made with a Sedigraph™ 5100 or 5120, Micromeritics Instrument Corporation. The method and the instrument are known to the skilled person and are commonly used to determine grain size of fillers and pigments. The measurement is carried out in an aqueous solution of 0.1 wt % $Na_4P_2O_7$. The samples were dispersed using a high speed stirrer and sonicated.

The processes and instruments are known to the skilled person and are commonly used to determine grain size of fillers and pigments.

The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 µm (~nm). The equilibration time used at each pressure step is 20 seconds. The sample material is sealed in a 5 $cm^3$ chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p. 1753-1764).

The total pore volume seen in the cumulative intrusion data can be separated into two regions with the intrusion data from 214 µm down to about 1-4 µm showing the coarse packing of the sample between any agglomerate structures contributing strongly. Below these diameters lies the fine interparticle packing of the particles themselves. If they also have intraparticle pores, then this region appears bi-modal, and by taking the specific pore volume intruded by mercury into pores finer than the modal turning point, i.e. finer than the bi-modal point of inflection, the specific intraparticle pore volume is defined. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the interparticle pore region and the intraparticle pore region, if present. Knowing the intraparticle pore diameter range it is possible to subtract the remainder interparticle and interagglomerate pore volume from the total pore volume to deliver the desired pore volume of the internal pores alone in terms of the pore volume per unit mass (specific pore volume). The same principle of subtraction, of course, applies for isolating any of the other pore size regions of interest.

Preferably, the surface-reacted calcium carbonate has an intra-particle intruded specific pore volume in the range from 0.1 to 2.3 cm$^3$/g, more preferably from 0.2 to 2.0 cm$^3$/g, especially preferably from 0.4 to 1.8 cm$^3$/g and most preferably from 0.6 to 1.6 cm$^3$/g, calculated from mercury porosimetry measurement.

The intra-particle pore size of the surface-reacted calcium carbonate preferably is in a range of from 0.004 to 1.6 μm, more preferably in a range of between 0.005 to 1.3 μm, especially preferably from 0.006 to 1.15 μm and most preferably of 0.007 to 1.0 μm, e.g. 0.004 to 0.16 μm determined by mercury porosimetry measurement.

According to an exemplary embodiment, the surface-reacted calcium carbonate has a volume median particle size $d_{50}$ from 1.5 to 15 μm, preferably from 1.5 to 2; a specific surface-area of from 30 to 140 m$^2$/g, preferably from 40 to 60 m$^2$/g, measured using nitrogen and the BET method; and an intra-particle intruded specific pore volume from 0.2 to 2.0 cm$^3$/g, preferably from 0.2 to 0.4 cm$^3$/g, calculated from mercury porosimetry measurement.

Due to the intra and interpore structure of the surface-reacted calcium carbonate, it can be a superior agent to deliver previously ad/absorbed materials over time relative to common materials having similar specific surface areas. Thus, generally, any agent fitting into the intra- and/or inter particle pores of the surface-reacted calcium carbonate is suitable to be transported by the surface-reacted calcium carbonate according to the invention. For example, active agents such as those selected from the group comprising pharmaceutically active agents, biologically active agents, disinfecting agents, preservatives, flavouring agents, surfactants, oils, fragrances, essential oils, and mixtures thereof can be used. According to one embodiment, at least one active agent is associated with the surface-reacted calcium carbonate.

According to one embodiment of the present invention, the surface-reacted calcium carbonate comprises an water-insoluble, at least partially crystalline calcium salt of an anion of the at least one acid, which is formed on the surface of the natural ground calcium carbonate or precipitated calcium carbonate. According to one embodiment, the water-insoluble, at least partially crystalline salt of an anion of the at least one acid covers the surface of the natural ground calcium carbonate or precipitated calcium carbonate at least partially, preferably completely. Depending on the employed at least one acid, the anion may be sulphate, sulphite, phosphate, citrate, oxalate, acetate, formate and/or chloride.

For example, the use of phosphoric acid, $H_2PO_4^-$ or $HPO_4^{2-}$ as the $H_3O^+$ ion donor may lead to the formation of hydroxylapatite. Therefore, in a preferred embodiment, the at least one water-insoluble calcium salt is hydroxylapatite.

According to one embodiment, the at least one water-insoluble calcium salt is hydroxylapatite, wherein the surface-reacted calcium carbonate provides a ratio of hydroxylapatite to calcite, aragonite and/or vaterite, preferably to calcite, in the range of from 1:99 to 99:1 by weight. Preferably, the surface-reacted calcium carbonate may provide a ratio of hydroxylapatite to calcite, aragonite and/or vaterite, preferably to calcite, in the range of from 1:9 to 9:1, preferably 1:7 to 8:1, more preferably 1:5 to 7:1 and most preferably 1:4 to 7:1 by weight.

In a similar manner, the use of other $H_3O^+$ ion donors may lead to the formation of corresponding water-insoluble calcium salts other than calcium carbonate on at least part of the surface of the surface-reacted calcium carbonate. In one embodiment, the at least one water-insoluble calcium salt is thus selected from the group consisting of octacalcium phosphate, hydroxylapatite, chlorapatite, fluorapatite, carbonate apatite and mixtures thereof, wherein the surface-reacted calcium carbonate shows a ratio of the at least one water-insoluble calcium salt to calcite, aragonite and/or vaterite, preferably to calcite, in the range of from 1:99 to 99:1, preferably from 1:9 to 9:1, more preferably from 1:7 to 8:1, even more preferably from 1:5 to 7:1 and most preferably from 1:4 to 7:1 by weight.

According to one embodiment the surface-reacted calcium carbonate comprises:
(i) a specific surface area of from 15 to 200 m$^2$/g measured using nitrogen and the BET method according to ISO 9277:2010, and
(ii) an intra-particle intruded specific pore volume in the range of from 0.1 to 2.3 cm$^3$/g calculated from mercury porosimetry measurement.

The Cosmetic Composition

According to one aspect of the present invention, a cosmetic composition having UV-A and/or UV-B protection comprising at least one inorganic UV filter, and surface-reacted calcium carbonate having a volume median particle size $d_{50}$ from 0.1 to 90 μm is provided, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

It is appreciated that the cosmetic composition may comprise the at least one inorganic UV filter and its amount in dependence of the cosmetic composition to be prepared and/or the manufacturer's needs and/or legal requirements.

According to one embodiment the at least one inorganic UV filter is present in an amount from 1 to 50 wt.-%, based on the total weight of the cosmetic composition, preferably from 2 to 40 wt.-%, more preferably from 5 to 30 wt.-%, and most preferably from 10 to 25 wt.-%, e.g. from 10 to 20 wt.-%, and/or the surface-reacted calcium carbonate is present in an amount from 0.1 to 50 wt.-%, based on the total weight of the cosmetic composition, preferably from 0.5 to 20 wt.-%, more preferably from 1 to 10 wt.-%, and most preferably from 3 to 6 wt.-%.

According to an exemplary embodiment, the cosmetic composition according to the present invention comprises 10 to 25 wt.-% of the least one inorganic UV filter, preferably zinc oxide and/or titanium dioxide, and 3 to 6 wt.-% of surface-reacted calcium carbonate. According to a preferred exemplary embodiment, the at least one inorganic UV filter comprises, preferably consists of, zinc oxide and titanium dioxide, wherein the surface of the zinc oxide is at least partially coated with triethoxycaprylsilane and the surface of the titanium dioxide is at least partially coated with aluminum oxide and dimethicone.

The inventors of the present invention surprisingly found that the sun protection factor (SPF) of cosmetic compositions comprising an inorganic UV filter can be boosted by adding to said composition a surface-reacted calcium carbonate having a volume median particle size $d_{50}$ from 0.1 to 90 μm. Thus, by adding said surface-reacted calcium carbonate it is possible to reduce the amount of inorganic UV filter, which is necessary in order to achieve a certain SPF. This may be in particular advantageous in case the inorganic UV filter is a nanosized material, since the amount of nanosized material, which may be present in cosmetic compositions, is regulated and limited in many countries.

Furthermore, it was surprisingly found that the sensory properties of cosmetic compositions comprising an inorganic UV filter can be improved by adding to said composition a surface-reacted calcium carbonate having a volume median particle size $d_{50}$ from 0.1 to 90 µm. For example, it was found that the inventive composition is less greasy and sticky compared to a composition having the same ingredients except for the surface-reacted calcium carbonate. Moreover, the inventive composition can spread more easily, form a more uniform film and dry faster, when applied on the skin. It was also found that the inventive composition shows a lower tendency to "whiten" the skin.

According to a further aspect of the present invention, use of surface-reacted calcium carbonate for boosting the sun protection factor (SPF) of a cosmetic composition having UV-A and/or UV-B protection and comprising at least one inorganic UV filter is provided, wherein the surface-reacted calcium carbonate has a volume median particle size $d_{50}$ from 0.1 to 90 µm, and the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

According to still a further aspect of the present invention, use of surface-reacted calcium carbonate for improving the sensory properties of a cosmetic composition having UV-A and/or UV-B protection and comprising at least one inorganic UV filter is provided, wherein the surface-reacted calcium carbonate has a volume median particle size $d_{50}$ from 0.1 to 90 µm, and the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

For the purpose of the present invention, the term "sensory properties" comprises the sensory parameters spreadability, whitening effect, greasiness, sticky feeling, and shiny residue. According to one embodiment, the surface-reacted calcium carbonate is used for improving the spreadability of a cosmetic composition having UV-A and/or UV-B protection and comprising at least one inorganic UV filter. Additionally or alternatively, the surface-reacted calcium carbonate is used for reducing the sticky feeling and/or greasiness and/or whitening effect of a cosmetic composition having UV-A and/or UV-B protection and comprising at least one inorganic UV filter. The sensory properties may be determined by a sensory analysis, e.g. as carried out by a trained panel.

The cosmetic composition of the present invention does not require the addition of organic UV filters in order to screen UV light over the whole UV-A and UV-B range. Thus, according to a preferred embodiment the cosmetic composition does not comprise an organic UV filter.

However, it would also be possible to combine the at least one inorganic UV filter and the surface-reacted calcium carbonate with an organic UV filter. According to one embodiment, the cosmetic composition further comprises at least one organic UV filter. The at least one organic UV filter may be selected from the group consisting of derivatives of cinnamic acid and its salts, derivatives of salicylic acid and its salts, benzophenones, derivatives of aminobenzoic acid and its salts, dibenzoylmethanes, benzylidenecamphor derivatives, benzimidazole derivatives, diphenylacrylate derivatives, acrylamide derivatives, benzotriazole derivatives, triazine derivatives, benzalmalonate derivatives, aminobenzoate derivatives, octocrylene, and mixtures thereof, preferably derivatives of cinnamic acid and its salts, benzophenones, octocrylene, and mixtures thereof.

It is appreciated that the cosmetic composition may comprise the at least one organic UV filter and its amount in dependence of the cosmetic composition to be prepared and/or the manufacturer's needs. According to one embodiment, the cosmetic composition comprises the at least one organic UV filter in an amount from 1 to 15 wt.-%, based on the total weight of the cosmetic composition, preferably from 2 to 10, wt.-%, and most preferably from 3 to 6 wt.-%.

The term "organic UV filter" as used herein refers to an organic material, which can absorb ultraviolet (UV) radiation in the UV-A and/or UV-B region of the electromagnetic spectrum, i.e. electromagnetic radiation having a wavelength between 290 and 400 nm.

The cosmetic composition may also comprise further additives. Additives that are suitable for cosmetic compositions are known to the skilled person and are described in, for example, Regulation EC No 1223/2009 of the European Parliament and of the Council of 30 Nov. 2009. According to one embodiment the cosmetic composition further comprises at least one additive selected from the group consisting of bleaching agents, thickeners, stabilizers, chelating agents, preserving agents, wetting agents, emulsifiers, emollients, fragrances, colorants, skin tanning compounds, antioxidants, pigments, oils, water, and mixtures thereof.

For example, the emulsifier can be an ionic emulsifier, more preferably and anionic or cationic emulsifier. The emulsifier can be of natural vegetable origin e.g. polyglycerol ester or synthetic. More preferably, the emulsifier may be selected from the group comprising PEG compounds, PEG-free emulsifier, silicone-based emulsifier, silicones, waxes and mixtures thereof. For example, the emulsifier may be selected from the group comprising PEG compounds such as PEG-8 myristate, PEG-30 glyceryl cocoate, PEG-80 glyceryl cocoate, PEG-15 soyamide/IPDI copolymer, PEG-40 sorbitan peroleate, PEG-150 stearate and mixtures thereof, carbomer, carboxymethylcellulose, ceresin (aka mineral wax), diethanolamine (DEA), isopropyl stearate, isopropyl laurate, isopropyl palmitate, isopropyl oleate, polysorbate 20, polysorbate 60, polysorbate 80, propylene glycol, sorbitan stearate, sorbitan laurate, sorbitan palmitate, sorbitan oleate, steareth-20, triethanolamine (TEA), beeswax, candelilla wax, carnauba wax, cetearyl alcohol, cetearyl wheat bran glycosides, cetearyl wheat straw glycosides, decyl glucoside, jojoba, lecithin, vegetable glycerin, xanthan gum, coco glucoside, coconut alcohol, arachidyl alcohol, behenyl alcohol, arachidyl glucoside, and mixtures thereof.

According to one embodiment, the emulsifier is a mixture of coco glucoside, coconut alcohol, arachidyl alcohol, behenyl alcohol and/or arachidyl glucoside.

The fragrance may be selected from a natural and/or synthetic fragrance known as being suitable in cosmetic formulations.

The colorant may be selected from a natural and/or synthetic colorant, pigment or dye such as $Fe_2O_3$, ZnO, mica, bismuth oxychloride, and mixtures thereof.

According to one embodiment, the skin tanning compound is preferably dihydroxyacetone (DHA) and/or erythrulose. For example, the skin tanning compound may be dihydroxyacetone (DHA) or erythrulose. Alternatively, the skin tanning compound may be dihydroxyacetone (DHA) in combination with erythrulose.

According to one embodiment, the wetting agent is preferably 1,3-propanediol.

According to one embodiment, the cosmetic composition further comprises at least one emollient. Examples of suitable emollients are isocetylstearoylstearate, ethylhexyl stearate, octyldodecyl stearoyl stearate, isocetyl stearate, isopropyl isostearate, isostearyl isostearate, ethylhexyl hydroxystearate, ethylhexyl palmitate, isopropyl palmitate, neopentyl glycol diheptanoate, ethylhexyl isononanoate, isononyl isononanoate, cetearyl isononanoate, cetearyl octanoate, diisopropyl adipate, dicapryl adipate, diisostearylmalate, decyl oleate, isodecyl oleate, diisopropyl myristate, isostearyl neopentanoate, octyl dodecyl neopentanoate, ethylhexyl cocoate, PEG-7 glyceril cocoate, C12-15 alkyl benzoate, C16-17 alkyl benzoate, stearyl benzoate, isostearyl benzoate, ethylhexyl benzoate, octyldodecyl benzoate, cocoglyceride, coconut alkanes, coco-caprylate/caprate, and mixtures thereof. For example, the cosmetic composition may further comprise a mixture of cocoglyceride, isononyl isononanoate, coconut alkanes and coco-caprylate/caprate as emollient.

Additionally or alternatively, the cosmetic composition further comprises at least one thickener. Examples of suitable thickener for a water-based dispersion are thickener based on silicate such as magnesium silicate, aluminium silicate and mixtures thereof, hydroxyethylcellulose or polyacrylamide. Preferably, the thickener in the water-based dispersion is based on silicate such as magnesium silicate, aluminium silicate and mixtures thereof, more preferably mixtures of magnesium and aluminium silicate. Examples of suitable thickener for an oil-based dispersion are selected from the group comprising silicate such as magnesium silicate, aluminium silicate, silica dimethylsilicate, hydrophobic fumed silica, polyacrylic acid, salts of polyacrylic acid, derivatives of polyacrylic acid, PEG compounds such as PEG-8 myristate, PEG-30 glyceryl cocoate, PEG-80 glyceryl cocoate, PEG-15 soyamide/IPDI copolymer, PEG-40 sorbitan peroleate, PEG-150 stearate and mixtures thereof, methyl cellulose, ethyl cellulose, propyl cellulose, carboxymethylcellulose, xanthan gum, ammonium acryloyldimethyltaurate/VP copolymer and mixtures thereof. For example, the cosmetic composition may further comprise ammonium acryloyldimethyltaurate/VP copolymer as thickener.

Additionally or alternatively, the cosmetic composition further comprises at least one preserving agent. Examples of suitable preserving agents are phenoxyethanol, ethylhexylglycerin, parabens such as methyl paraben, ethyl paraben, propyl paraben, butyl paraben and mixtures thereof, benzoic acid, sodium benzoate, sorbic acid, potassium sorbate and mixtures thereof. For example, said mixture may comprise phenoxyethanol and ethylhexylglycerin in a weight ratio of phenoxyethanol to ethylhexylglycerin from 10:1 to 1:1, more preferably from 10:1 to 3:1 and most preferably from 10:1 to 7:1 such as of about 9:1.

The stabilizers may be an extract from *Larix* species. Examples of extracts from *Larix* species include extracts from *Larix decidua* such as *Larix decidua* Mill. var. *decidua, Larix decidua* var. *polonica, Larix occidentalis, Larix gmelinii* such as *Larix gmelinii* var. *gmelinii, Larix gmelinii* var. *japonica, Larix gmelinii* var. *principis-rupprechtii, Larix gmelinii* var. *olgensis, Larix graffithii* such as *Larix graffithii* var. *graffithii, Larix graffithii* var. *speciosa, Larix kaempferi, Larix potaninii* such as *Larix potaninii* var. *australis, Larix potaninii* var. *macrocarpa, Larix potaninii* var. *chinensis, Larix potaninii* var. *australis, Larix potaninii* var. *himalaica, Larix potaninii* var. *potaninii, Larix sibirica, Larix laricina, Larix lyallii, Larix* x *eurokurilensis, Larix* x *eurolepis, Larix* x *marschlinsii, Larix* x *pendula*, and mixtures thereof.

Examples of suitable chelating agents are a polyphosphate, ethylenediamine-N,N,N',N'-tetraacetic acid (EDTA), pyridine-2,6-dicarboxylic acid (DPA), diethylenetriaminepentaacetic acid (DTPA), N,N-bis(carboxymethyl)glycine (NTA), ammonium diethyldithiophosphate (DDPA), disodium ethylenediamine-tetraacetate ($Na_2H_2EDTA$), calcium-disodium-ethylenediamine-tetraacetate ($CaNa_2EDTA$), citric acid and salts of citric acid, sodium gluconate, and mixtures thereof.

Examples of suitable wetting agents are primary alcohols such as 1-ethanol, 1-propanol, 1-butanol, isobutanol 1-pentanol, isoamyl alcohol, 2-methyl-1 butanol, 1-hexanol, 1-heptanol, 1-octanol, 1-nonanol, 1-decanol, 1-undecanol, 1-dodecanol, 1-tridecanol, 1-tetradecanol, 1-pentadecanol, cetyl alcohol, 1-heptadecanol, stearyl alcohol, 1-nonadecanol and mixtures thereof, secondary alcohols such as isopropanol, 2-butanol, 2-pentanol, 2-hexanol, 2-heptanol and mixtures thereof, tertiary alcohols such as tert.-butyl alcohol, tert.-amyl alcohol, 2-methyl-2-pentanol, 2-methylhexan-2-ol, 2-methylheptan-2-ol, 3-methyl-3-pentanol, 3-methyloctan-3-ol and mixtures thereof, diols such as 1,2-diols or 1,3-diols, e.g. 1,3-propandiol, urea, and mixtures thereof.

Examples of suitable antioxidants are butylhydroxyanisol (BHA), butylhydroxytoluol (BHT), gallate, carotinoid, polyphenols such as resveratrol, flavonoid and mixtures thereof, derivatives of polyphenols, ascorbic acid and salts thereof, tocopherol and salts thereof, betacarotin, ubichinon, tocotrienol, dihydroquercetin, antioxidants of natural origin, and mixtures thereof.

Any oil known to the skilled person as being suitable in cosmetic formulations may be used. For example, the oil may be selected from the group comprising alkanecoconutester, polydimethylsiloxanes, polyalkylmethylsiloxanes, silicones, vegetable oils such as palm oil, esters of vegetable oils, and mixtures thereof. Preferably, the at least one oil is alkanecoconutester.

Examples of suitable pigments are inorganic red pigments such as iron oxide, ferric hydroxide and iron titanate, inorganic brown pigments such as γ-iron oxide, inorganic yellow pigments such as yellow iron oxide and yellow ocher, inorganic black pigments such as black iron oxide and carbon black, inorganic purple pigments such as manganese violet and cobalt violet, inorganic green pigments such as chromium hydroxide, chrome oxide, cobalt oxide and cobalt titanate, inorganic blue pigments such as iron blue and ultramarine, particulate powders such as particulate titanium oxide, particulate cerium oxide and particulate zinc oxide, laked tar dyes, laked natural dyes, and synthetic resin powders combining foregoing powders.

The bleaching agent may be selected from one or more of a vitamin B3 compound or its derivative e.g. niacin, nicotinic acid or niacinamide or other well-known bleaching agents e.g. adapalene, aloe extract, ammonium lactate, anethole derivatives, apple extract, arbutin, azelaic acid, kojic acid, bamboo extract, bearberry extract, bletilla tuber, bupleurum falcatum extract, burnet extract, butyl hydroxy anisole, butyl hydroxy toluene, citrate esters, Chuanxiong, Dang-Gui, deoxyarbutin, 1,3-diphenyl propane derivatives, 2,5-dihydroxybenzoic acid and its derivatives, 2-(4-acetoxyphenyl)-1,3-dithane, 2-(4-hydroxyphenyl)-1,3-dithane, ellagic acid, escinol, estragole derivatives, Fadeout (Pentapharm), Fangfeng, fennel extract, ganoderma extract, gaoben, Gatuline Whitening (Gattlefosse), genistic acid and its derivatives, glabridin and its derivatives, gluco pyranosyl-1-ascorbate, gluconic acid, glycolic acid, green tea extract, 4-hydroxy-5-methyl-3[2H]-furanone, hydroquinone, 4-hydroxyanisole and its derivatives, 4-hydroxy benzoic acid derivatives, hydroxycaprylic acid, inositol ascorbate, lemon extract, linoleic acid, magnesium ascorbyl phosphate, Melawhite (Pentapharm), morns alba extract, mulberry root extract, 5-octanoyl salicylic acid, parsley extract, phellinus linteus extract, pyrogallol derivatives, 2,4-resorcinol derivatives, 3,5-resorcinol derivatives, rose fruit extract, salicylic acid, Song-Yi extract, 3,4,5-trihydroxybenzyl derivatives, tranexamic acid, vitamins like vitamin B6, vitamin B12, vitamin C, vitamin A, dicarboxylic acids, resorcinol derivatives, extracts from plants viz. rubia and symplocos, hydroxycarboxylic acids like lactic acid and their salts e.g. sodium lactate, and mixtures thereof. Vitamin B3 compound or its derivative e.g. niacin, nicotinic acid or niacinamide are the more preferred bleaching agents, most preferred being niacinamide. Niacinamide, when used, is preferably present in an amount in the range of 0.1 to 10 wt.-%, more preferably 0.2 to 5 wt.-%, based on the total weight of the cosmetic composition.

It is appreciated that the cosmetic composition may comprise the at least one further additive and its amount in dependence of the cosmetic composition to be prepared and/or the manufacturer's needs. For example, the cosmetic composition may comprise 0.1 to 50 wt.-% of oils and/or water, and/or 0.1 to 10 wt.-% of thickeners, stabilizers, chelating agents, bleaching agents, wetting agents, emulsifiers, emollients, and/or skin tanning compounds, and/or 0.1 to 3 wt.-% of preserving agents, fragrances, colorants, antioxidants, pigments, wherein the wt.-% is based on the total weight of the cosmetic composition.

The cosmetic composition may be a lotion, spray, gel or other topical product. According to one embodiment cosmetic composition is a sunscreen product, an eye make-up product, a facial make-up product, a lip care product, a hair care product, a hair styling product, a nail care product, a hand care product, a skin care product, or a combination product thereof.

Preferably, the cosmetic composition is selected from a sunscreen product such as sunblock lotion or sunblock cream, suntan lotion or suntan cream, sunburn lotion or sunburn cream, sun cream or sun lotion, after sun lotion or after sun cream, sun lip balm and the like, eye makeup product such as brow liner, eye liner, eye shadow, eye mascara and the like, facial makeup product such as foundation, concealer, rouge, contour powder/creams, bronzer and the like, lip care product such as lipstick, lip balm, lip gloss, lip liner, lip plumper, lip conditioner, lip primer, lip booster and the like, hair care product such as hair serum, shampoo, dry powder shampoo, conditioner such as leave-in conditioner, hair color, hair loss products, heat protection spray and the like, hair styling product such as hair wax, hair mousse, pomade, hair gel, hair spray, styling paste, glue, hair volumizer, hair tonic and the like, nail care product or hand care product such as nail polish, lacquer, nail polish remover, nail oil and the like, skin care product such as body lotion, body cream, bronzer, hand cream, hand lotion, foot cream, face cream, face lotion, day and night creams, bb creams, cc creams, dd creams and the like, and mixtures thereof. For example, the cosmetic composition may be a sunscreen product, eye makeup product, facial makeup product, lip care product, hair care product, hair styling product, nail care product, hand care product, skin care product, or combination product, which is provided with a sun protective factor such as a SPF of 10, 15, 20, 25, 30, 40, 50 or more.

Method of Producing the Cosmetic Composition

According to another aspect of the present invention, a method for producing a cosmetic composition is provided, wherein at least one inorganic UV filter is mixed with surface-reacted calcium carbonate having a volume median particle size $d_{50}$ from 0.1 to 90 µm, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

The at least one inorganic UV filter may be provided in form of a powder or in form of a dispersion.

The term "dispersion" in the meaning of the present invention refers to a system comprising a dispersing medium or solvent and at least one inorganic particulate material, wherein at least a part of the particles of the at least one inorganic particulate material are present as insoluble solids or suspended particles in the dispersing medium or solvent.

The surface-reacted calcium carbonate may be provided in any suitable liquid or dry form. For example, the surface-reacted calcium carbonate may be in form of a powder and/or a suspension. The suspension can be obtained by mixing the surface-reacted calcium carbonate with a solvent, preferably water. The surface-reacted calcium carbonate to be mixed with a solvent, and preferably water, may be provided in any form, for example, as suspension, slurry, dispersion, paste, powder, a moist filter cake or in pressed or granulated form.

The suspension can be undispersed or dispersed, i.e. the suspension includes a dispersant, and thus, forms a dispersion, e.g. an aqueous dispersion. Suitable dispersants are known in the art, and may be selected, e.g., from polyelectrolytes, polyhydroxystearic acid, acetlyacetone, propylamine, oleic acid, polyacrylates, carboxymethylcellulose based dispersants, and mixtures thereof.

According to one embodiment of the present invention, the solids content of the suspension, preferably aqueous suspension, of the surface-reacted calcium carbonate is from 1 to 85 wt.-%, more preferably from 5 to 75 wt.-%, and most preferably from 10 to 40 wt.-%, based on the total weight of the suspension.

In case the surface-reacted calcium carbonate is provided in dry form, the moisture content of the surface-reacted calcium carbonate can be between 0.01 and 5 wt.-%, based on the total weight of the surface-reacted calcium carbonate. According to one embodiment, the moisture content of the surface-reacted calcium carbonate is less than or equal to 1.0 wt.-%, based on the total weight of the surface-reacted calcium carbonate, preferably less than or equal to 0.5 wt.-%, and more preferably less than or equal to 0.2 wt.-%. According to another embodiment, the moisture content of the surface-reacted calcium carbonate is between 0.01 and 0.15 wt.-%, preferably between 0.02 and 0.10 wt.-%, and more preferably between 0.03 and 0.07 wt.-%, based on the total weight of the surface-reacted calcium carbonate.

The mixing of the at least one inorganic UV filter and the surface-reacted calcium carbonate may be carried out in any order in any manner known by the skilled person. The mixing may be carried out under conventional mixing conditions. The skilled man will adapt these mixing conditions (such as the configuration of mixing pallets and mixing speed) according to his process equipment. It is appreciated that any mixing method which would be suitable to form a cosmetic composition may be used.

In one embodiment, mixing is carried out at temperatures typically used for preparing a cosmetic base formulation. Preferably, mixing is carried out at a temperature in the range from 15 to 100° C., more preferably from 20 to 85° C. such as of about 45° C.

In case the cosmetic composition further comprises at least one organic UV filter and/or at least one additive, said at least one organic UV filter and/or at least one additive may be added before, during, or after mixing the at least one inorganic UV filter and the surface-reacted calcium carbonate.

The scope and interest of the invention will be better understood based on the following examples which are intended to illustrate certain embodiments of the present invention and are non-limitative.

EXAMPLES

1. Measurement Methods

In the following, measurement methods implemented in the examples are described.

Particle Size Distribution

Volume determined median particle size $d_{50}$ (vol) and the volume determined top cut particle size $d_{98}$ (vol) was evaluated using a Malvern Mastersizer 2000 Laser Diffraction System (Malvern Instruments Plc., Great Britain). The $d_{50}$ (vol) or $d_{98}$ (vol) value indicates a diameter value such that 50% or 98% by volume, respectively, of the particles have a diameter of less than this value. The raw data obtained by the measurement was analyzed using the Mie theory, with a particle refractive index of 1.57 and an absorption index of 0.005. The methods and instruments are known to the skilled person and are commonly used to determine particle size distributions of fillers and pigments.

The weight determined median particle size $d_{50}$ (wt) was measured by the sedimentation method, which is an analysis of sedimentation behaviour in a gravimetric field. The measurement was made with a Sedigraph™ 5100 or 5120 of Micromeritics Instrument Corporation, USA. The method and the instrument are known to the skilled person and are commonly used to determine particle size distributions of fillers and pigments. The measurement was carried out in an aqueous solution of 0.1 wt.-% $Na_4P_2O_7$. The samples were dispersed using a high speed stirrer and supersonicated.

Specific Surface Area (SSA)

The specific surface area was measured via the BET method according to ISO 9277 using nitrogen, following conditioning of the sample by heating at 250° C. for a period of 30 minutes. Prior to such measurements, the sample was filtered within a Buchner funnel, rinsed with deionised water and dried overnight at 90 to 100° C. in an oven. Subsequently, the dry cake was ground thoroughly in a mortar and the resulting powder was placed in a moisture balance at 130° C. until a constant weight was reached.

Intra-Particle Intruded Specific Pore Volume (in $cm^3/g$)

The specific pore volume was measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step was 20 seconds. The sample material was sealed in a 5 $cm^3$ chamber powder penetrometer for analysis. The data were corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine inter-particle packing of the particles themselves. If they also have intra-particle pores, then this region appears bi-modal, and by taking the specific pore volume intruded by mercury into pores finer than the modal turning point, i.e. finer than the bi-modal point of inflection, the specific intra-particle pore volume is defined. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the inter-particle pore region and the intra-particle pore region, if present. Knowing the intra-particle pore diameter range it is possible to subtract the remainder inter-particle and inter-agglomerate pore volume from the total pore volume to deliver the desired pore volume of the internal pores alone in terms of the pore volume per unit mass (specific pore volume). The same principle of subtraction, of course, applies for isolating any of the other pore size regions of interest.

UV Measurement for the Determination of the Sun Protection Factor ("SPF") and the UVA Protection Level (UVA PF)

The measurement was carried out according to EN ISO 24443: 2012 (Determination of sunscreen UVA photoprotection in vitro).

For the measurement a Kontron® spectrophotometer equipped with an UV source and a monochromator was used. The spectrophotometer is able to deliver a flow of energy between 290 and 400 nanometers.

Sample Preparation

For the UV measurements PMMA (Poly(methyl methacrylate) plates (Sunplates, supplied by Helioscience/Europlast, France) were used as a substrate for the formulations.

Small spots of the formulation to be analysed have been placed all over the surface of the PMMA plate. The quantity of formulation applied to the PMMA plates were approximately 1.3 mg/$cm^2$ and controlled by weighting. Then the small spots of formulation were transformed into a film that should be as homogeneous as possible.

The spectrophotometer was calibrated on the PMMA reference plates to ensure the quality of the results. Then the UV spectra of the PMMA plates with the homogeneous formulation films were measured in intervals of 1 nm starting from 290 nm to 400 nm.

Calculation of SPF and UVA PF

The SPF (in vitro) and the UVA PF (in vitro) have been calculated from the measured UV curves according to the following equations:

$$SPF \text{ in vitro} = \frac{\sum_{290\,nm}^{400\,nm} E(\lambda) \cdot S(\lambda) \cdot d\lambda}{\sum_{290\,nm}^{400\,nm} E(\lambda) \cdot S(\lambda) \cdot T(\lambda) \cdot d\lambda} \text{ and}$$

$$UVA\ PF \text{ in vitro} = \frac{\sum_{320\,nm}^{400\,nm} E(\lambda) \cdot S(\lambda) \cdot d\lambda}{\sum_{320\,nm}^{400\,nm} E(\lambda) \cdot S(\lambda) \cdot T(\lambda) \cdot d\lambda}$$

where $S(\lambda)$ is the solar irradiance spectrum, $E(\lambda)$ is a wave function that specifies the reactivity of the skin in function of the wave length, that means the erythemal action spectrum, and $T(\lambda)$ is the transmission in function of the wave length.

Sensory Evaluation

The sensory evaluation was carried out by a panel. The panel consisted of 4 members. Among these four members, two have degrees in beauty institute protocols.

The evaluation criteria were adapted to the texture, perfectly defined to the panelists before the analysis, and are the following:

Spreading: during product application, there is no resistance to movement. (Upper limit).

Non-spreading: during product application, there is resistance to movement. (Lower limit).

Whitening effect: during product application, the product whitens the skin. (Upper limit).

Non whitening: during product application, the product does not whiten the skin. (Lower limit).

Greasy (1 minute after spreading): when performing a rubbing motion, there is no resistance. The product facilitates movement. (Upper limit).

Dry (1 minute after spreading): when performing a rubbing motion, there is a resistance. The product inhibits the movement of the fingers without giving oily appearance to the skin. (Lower limit).

Sticky feeling (1 minute after spreading): by pressure movements on the skin with the index an adhesion is felt. (Upper limit).

Non sticky feeling (1 minute after spreading): by pressure movements on the skin with the index no adhesion is felt. (Lower limit).

Shiny residue (1 minute after spreading): which throws light, which shines. (Upper limit).

Non shiny residue (1 minute after spreading): which does not throw light, which does not shine, which has a matte finish. (Lower limit).

For sensory evaluation, a rating system (1 to 4=less pronounced to the more pronounced) was set up to facilitate the operation, and an evaluation grid was provided to the panel during the evaluation (see Table 1 below).

TABLE 1

Evaluation grid provided to the panel.

| Product analyzed: | from least | | | to most |
|---|---|---|---|---|
| Criteria | 1 | 2 | 3 | 4 |
| Spreading | | | | |
| Whitening effect | | | | |
| Greasy (after 1 minute) | | | | |
| Sticky feeling (after 1 minute) | | | | |
| Shiny residue (after 1 minute) | | | | |

Comments:

The sensory and organoleptic analysis made by the panel was carried on the underside of the forearm by placing a dab of cream for each assay using a spatula, then the product was applied with the fingers. The size of the applied amount of cream is reproducible for a given tester.

The assays were tested versus the reference product, indicated as such to the panel, by series of 5 (reference product included).

All sensory analyses were performed blind in a quiet room. Someone, who was not a part of the panel, prepared the product samples to be tested in plastic pots of 200 mL labeled from 1 to 10. There was no other indication on the samples.

2. Pigment Materials

In the following the INCI name of some ingredients will be used. INCI stands for International Nomenclature of Cosmetic Ingredients.

Surface-Reacted Calcium Carbonate 1 (SRCC 1)

SRCC 1 had a $d_{50}$ (vol)=1.9 μm, SSA=50.4 m$^2$/g with an intra-particle intruded specific pore volume of 0.319 cm$^3$/g (for the pore diameter range of 0.004 to 0.16 μm).

SRCC 1 was obtained by preparing 7 litres of an aqueous suspension of ground calcium carbonate in a mixing vessel by adjusting the solids content of a ground marble calcium carbonate from Kemal Pasha, Turkey, having a weight based median particle size distribution of 90% less than 1 μm, as determined by sedimentation, such that a solids content of 15 wt.-%, based on the total weight of the aqueous suspension, was obtained.

Whilst mixing the slurry, 3.5 kg of an aqueous solution containing 10 wt.-% phosphoric acid was added to said suspension over a period of 60 minutes at a temperature of 70° C. After the addition of the acid, the slurry was stirred for additional 5 minutes, before removing it from the vessel and drying.

Titanium Dioxide

A surface-treated, slightly hydrophobic ultrafine rutile titanium dioxide, sold under the tradename UV-TITAN M262, purchased from Merck. INCI name=titanium dioxide, alumina, dimethicone. Properties: 89% TiO$_2$, 6% Al$_2$O$_3$, 2% dimethicone.

Zinc Oxide

A surface-treated microfine zinc oxide for cosmetic applications, sold under the tradename Zano® 10 Plus, purchased from IMCD. INCI name=zinc oxide (and) triethoxycaprylyl silane.

3. Other Materials—Tradenames/Suppliers/INCI Names of Ingredients

TABLE 2

Other materials - tradenames/suppliers/INCI names of ingredients.

| Phase | Trade Name | INCI Name |
|---|---|---|
| Phase A | Bentone Gel IHD V (SACI-CFPA) | Isohexadecane & Disteardimonium Hectorite & Propylene Carbonate |
| | Dub ININ (Stearinerie Dubois) | Isononyl Isononanoate |
| | Creasil IH CG (The Innovation Company) | Isohexadecane |
| | UV Titan M262 (Merck) | Titanium Dioxide [nano] & Alumina & Dimethicone & Aqua |
| | Surface-reacted calcium carbonate (Omya) | |
| | Abil WE 09 (Evonik Goldschmidt) | Polyglyceryl-4 Isostearate & Cetyl PEG/PPG-10/1 Dimethicone Hexyl Laurate |

TABLE 2-continued

Other materials - tradenames/suppliers/INCI names of ingredients.

| Phase | Trade Name | INCI Name |
|---|---|---|
| | Abil WAX 9801 (Evonik Goldschmidt) | Cetyl Dimethicone |
| | Zano 10 PLUS (IMCD) | Zinc Oxide & Triethoxycaprylylsilane |
| | NHS-C339001-10 (Miyoshi) | CI 77492 & Isostearyl Sebacate & Disodium Stearoyl Glutamate & Aluminum Hydroxide |
| | NHS-C338001-10 (Miyoshi) | CI 77491 & Isostearyl Sebacate & Disodium Stearoyl Glutamate & Aluminum Hydroxide |
| | NHS-C337001-10 (Miyoshi) | CI 77499 & Isostearyl Sebacate & Disodium Stearoyl Glutamate & Aluminum Hydroxide |
| Phase B | Demineralized Water | Aqua |
| | Glycerine Codex (Interchimie) | Glycerin |
| | Zemea Propanediol (IMCD) | Propanediol |
| | Chlorphenesin BP 73 (Azelis) | Chlorphenesin & Aqua |
| | Phenoxetol (Clariant) | Phenoxyethanol |
| | Salt (Salins Du Midi) | Sodium Chloride |
| | Magnesium Sulfate Heptahydrate (Cooper) | Magnesium Sulfate |

4. Examples

Preliminary Study

A preliminary study was performed in order to determine if the surface-reacted calcium carbonate used in the present application on its own shows intrinsic inorganic UV filter properties. The outcome of this study was negative, this means that the surface-reacted calcium carbonate used has no intrinsic inorganic UV filter properties.

Sun Protection Factor Boosting Study

The influence of surface-reacted calcium carbonate on the sun protection factor (SPF) values in a test formulation was evaluated.

In this regard two series of tests were performed:

A. Substitution Case

The first series of tests was carried out with a reference formulation containing 20 wt.-% of surface-treated titanium dioxide UV Titan M262. Then the surface-reacted calcium carbonate was tested in substitution of the surface-treated titanium dioxide dose at 3% and 6%, in order to evaluate if the efficiency is dose dependent.

600 g formulation was prepared for each reference. The compositions of the formulations are listed in Table 3 below. The percentages refer to weight percentages.

TABLE 3

Composition of formulations for substitution case.

| Phase | INCI Name | Example 1 (comparative) | Example 2 | Example 3 |
|---|---|---|---|---|
| Phase A | Isohexadecane & disteardimonium hectorite & propylene carbonate | 3.00% | 3.00% | 3.00% |
| | Isononyl isononanoate | 11.0% | 11.0% | 11.0% |
| | Isohexadecane | 7.00% | 7.00% | 7.00% |
| | Titanium dioxide [nano] & alumina & dimethicone & aqua | 20.00% | 17.00% | 14.00% |

TABLE 3-continued

Composition of formulations for substitution case.

| Phase | INCI Name | Example 1 (comparative) | Example 2 | Example 3 |
|---|---|---|---|---|
| | Surface-reacted calcium carbonate | — | 3.00% | 6.00% |
| | Polyglyceryl-4 isostearate & cetyl PEG/PPG-10/1 dimethicone hexyl laurate | 7.00% | 7.00% | 7.00% |
| | Cetyl dimethicone | 1.50% | 1.50% | 1.50% |
| | Zinc oxide & triethoxycaprylylsilane | 7.00% | 7.00% | 7.00% |
| | CI 77492 & isostearyl sebacate & disodium stearoyl glutamate & aluminum hydroxide | 0.58% | 0.58% | 0.58% |
| | CI 77491 & isostearyl sebacate & disodium stearoyl glutamate & aluminum hydroxide | 0.09% | 0.09% | 0.09% |
| | CI 77499 & isostearyl sebacate & disodium stearoyl glutamate & aluminum hydroxide | 0.03% | 0.03% | 0.03% |
| Phase B | Aqua (demin. water) | 36.55% | 36.55% | 36.55% |
| | Glycerin | 2.00% | 2.00% | 2.00% |
| | Propanediol | 3.00% | 3.00% | 3.00% |
| | Chlorphenesin & aqua | 0.25% | 0.25% | 0.25% |
| | Phenoxyethanol | 0.15% | 0.15% | 0.15% |
| | Sodium chloride | 0.80% | 0.80% | 0.80% |
| | Magnesium sulfate | 0.05% | 0.05% | 0.05% |

The formulations were prepared as follows:

In a separate container the Bentone Gel IHD V (Isohexadecane & Disteardimonium Hectorite & Propylene Carbonate) was placed. Under strong stirring by using a VMI Supertest (from VMI, The mixing company, France), one by one, the components of phase A were added. A stirring time of 10 minutes was applied before adding a new component of phase A. After the addition of the last component of phase A the resulting mixture was blended for 1 minute at 9500 rpm by using an UltraTurrax (IKA-Werke GmbH & CO. KG, Germany).

In another container, the components of phase B were weighed one by one under stirring using a VMI Supertest. The resulting mixture was stirred until a homogeneous phase was obtained.

Then, while stirring by using a VMI Supertest, the mixture of phase B was slowly added to the mixture of phase A. Stirring was continued until a homogeneous phase was obtained.

The homogeneous products were then used for UV tests and sensory analysis. The results of the UV tests are listed in Table 5 below.

B. Addition Case

The second series of tests was carried out with a "placebo" formulation containing 10 wt.-% of surface-treated titanium dioxide UV Titan M262. Then the surface-reacted calcium carbonate was tested in addition of the surface-treated titanium dioxide dose at 3% and 6%, in order to evaluate if the efficiency is dose dependent.

600 g formulation was prepared for each reference. The compositions of the formulations are listed in Table 4 below. The percentages refer to weight percentages.

TABLE 4

Composition of formulations for addition case.

| Phase | INCI Name | Example 4 (comparative) | Example 5 | Example 6 |
|---|---|---|---|---|
| Phase A | Isohexadecane & disteardimonium hectorite & propylene carbonate | 3.00% | 3.00% | 3.00% |
| | Isononyl isononanoate | 11.0% | 11.0% | 11.0% |
| | Isohexadecane | 7.00% | 7.00% | 7.00% |
| | Titanium dioxide [nano] & alumina & dimethicone & aqua | 10.00% | 10.00% | 10.00% |
| | Surface-reacted calcium carbonate | — | 3.00% | 6.00% |
| | Polyglyceryl-4 isostearate & cetyl PEG/PPG-10/1 dimethicone hexyl laurate | 7.00% | 7.00% | 7.00% |
| | Cetyl dimethicone | 1.50% | 1.50% | 1.50% |
| | Zinc oxide & triethoxycaprylylsilane | 7.00% | 7.00% | 7.00% |
| | CI 77492 & isostearyl sebacate & disodium stearoyl glutamate & aluminum hydroxide | 0.58% | 0.58% | 0.58% |
| | CI 77491 & isostearyl sebacate & disodium stearoyl glutamate & aluminum hydroxide | 0.09% | 0.09% | 0.09% |
| | CI 77499 & isostearyl sebacate & disodium stearoyl glutamate & aluminum hydroxide | 0.03% | 0.03% | 0.03% |
| Phase B | Aqua (demin. water) | 46.55% | 43.55% | 40.55% |
| | Glycerin | 2.00% | 2.00% | 2.00% |
| | Propanediol | 3.00% | 3.00% | 3.00% |
| | Chlorphenesin & aqua | 0.25% | 0.25% | 0.25% |
| | Phenoxyethanol | 0.15% | 0.15% | 0.15% |
| | Sodium chloride | 0.80% | 0.80% | 0.80% |
| | Magnesium sulfate | 0.05% | 0.05% | 0.05% |

The formulations were prepared according to the method described for the substitution case above.

The homogeneous products were then used for UV tests and sensory analysis. The results of the UV tests are listed in Table 6 below.

Results of Sun Protection Factor Boosting Study
A. Substitution Case

TABLE 5

Results of UV test for the substitution case.

| Example | SPF value | UVA PF | SPF/UVA PF Ratio | Continuous wave [nm] |
|---|---|---|---|---|
| 1 (w/o any calcium carbonate; 20% TiO₂) | 52.5 | 15.1 | 3.47 | 375 |
| 2 (3% surface-reacted calcium carbonate) | 117 | 26.4 | 4.45 | 375 |
| 3 (6% surface-reacted calcium carbonate) | 68.8 | 18.5 | 3.72 | 375 |
| PMMA plate reference | 25.7 | 8.9 | Not applicable | Not applicable |

The above results show that the surface-reacted calcium carbonate has SPF booster properties in UVA or UVB. It can be derived from the above Table that the formulations in which the titan dioxide was substituted by 3% of surface-reacted calcium carbonate shows higher SPF values and UVA PF (protection factor) than the mixtures where the titan dioxide was substituted by 6% of surface-reacted calcium carbonate. When the titan dioxide is substituted by 3% of the surface-reacted calcium carbonate the SPF values is more than doubled.

As already determined the surface-reacted calcium carbonate used does not possess UV filter properties. Hence, without wishing to be bound to any theory it is believed that the booster effect of the surface-reacted calcium carbonate is due to their particle size. They fill the gap between the titan dioxide and zinc oxide particle in the formulation and as a consequence boost the SPF values.

B. Addition Case

TABLE 6

Results of UV test for the addition case.

| Example | SPF value | UVA PF | SPF/UVA PF Ratio | Continuous wave [nm] |
|---|---|---|---|---|
| 4 (w/o any calcium carbonate; 10% TiO₂) | 34.4 | 12.9 | 2.66 | 375 |
| 5 (3% surface-reacted calcium carbonate) | 57.2 | 18.2 | 3.15 | 375 |
| 6 (6% surface-reacted calcium carbonate) | 53.8 | 18.1 | 2.97 | 375 |
| PMMA plate reference | 25.7 | 8.9 | Not applicable | Not applicable |

The above results show that the surface-reacted calcium carbonate has SPF booster properties in UVA or UVB. It can be derived from the above Table that formulations in which 3% of surface-reacted calcium carbonate were added to the titan dioxide show higher SPF values and UVA PF (protection factor) than the mixtures where 6% of surface-reacted calcium carbonate were added to the titan dioxide.

Sensory Evaluation
A. Substitution Case

The results of the panel compiled in Table 7 below, show that the formulations, in which the titan dioxide was replaced by 3% and 6% of the surface-reacted calcium carbonate (Examples 2 & 3) were less greasy and sticky compared to the formulation of Example 1. The spreadability was better with the surface-reacted calcium carbonate (Examples 3 & 5). It has the advantage to provide a silky touch. The whitening effect was increased by the formulations, in which the titan dioxide was replaced by 3% and 6% of the surface-reacted calcium carbonate (Examples 2 & 3). In all cases the cream entered into the skin and left no residues on the surface. The skin was soft and shiny.

TABLE 7

Results of sensory evaluation for the substitution case.

| Criteria | Example 1 (comparative) | Example 2 | Example 3 |
|---|---|---|---|
| Spreading | 3 | 3.2 | 3.3 |
| Whitening effect | 1.6 | 2.25 | 2.25 |
| Greasy (after 1 minute) | 2.25 | 2.5 | 1.8 |
| Sticky feeling (after 1 minute) | 1.75 | 1.6 | 1.4 |
| Shiny residue (after 1 minute) | 2.5 | 2.4 | 2 |

B. Addition Case

The results of the panel compiled in Table 8 below, show that the formulations, in which 3% and 6% of the surface-reacted calcium carbonate (Examples 5 & 6) were added to the 10% TiO₂ were less greasy and sticky compared to the formulation of Example 4. The formulation dried faster when applied on the skin when it contained 6% surface-reacted calcium carbonate (Example 6). The whitening effect was lower with the surface-reacted calcium carbonate (Examples 5 & 6). It has the advantage to provide a silky touch.

TABLE 8

Results of sensory evaluation for the addition case.

| Criteria | Example 4 (comparative) | Example 5 | Example 6 |
|---|---|---|---|
| Spreading | 2.6 | 2.4 | 2.5 |
| Whitening effect | 2.4 | 2.1 | 2.25 |
| Greasy (after 1 minute) | 2.5 | 2.5 | 1.9 |
| Sticky feeling (after 1 minute) | 1.8 | 1.5 | 1.75 |
| Shiny residue (after 1 minute) | 2.1 | 2 | 1.9 |

From the above results it can be concluded that the surface-reacted calcium carbonate used provides an improved sensory feeling by improving or reducing the criteria like greasiness, stickiness and spreadability. Moreover, the whitening effect may be reduced.

The invention claimed is:

1. A cosmetic composition comprising:
at least one inorganic UV filter; and
surface-reacted calcium carbonate having a volume median particle size $d_{50}$ from 0.1 to 90 μm and an intra-particle intruded specific pore volume from 0.2 to 2.0 cm$^3$/g, calculated from mercury porosimetry measurement;
wherein
hydroxyapatite is formed on the surface of natural ground calcium carbonate and at least partially covers the surface of the natural ground calcium carbonate, and
is a reaction product of natural ground calcium carbonate with carbon dioxide and phosphoric acid,
the cosmetic composition provides UV-A and/or UV-B protection, and
the surface-reacted calcium carbonate particles are preformed prior to combination with the UV filter particles.

2. The cosmetic composition of claim 1, wherein the at least one inorganic UV filter is selected from the group consisting of titanium dioxide, zinc oxide, iron oxide, hydroxyapatite, cerium oxide, calcium-doped cerium oxide, cerium phosphate, and mixtures thereof.

3. The cosmetic composition of claim 1, wherein the at least one inorganic UV filter is in form of particles having a weight median particle size $d_{50}$ from 10 to 1 000 nm.

4. The cosmetic composition of claim 1, wherein the at least one inorganic UV filter is present in an amount from 1 to 50 wt.-%, based on the total weight of the cosmetic composition.

5. The cosmetic composition of claim 1, wherein the surface-reacted calcium carbonate has a volume median particle size $d_{50}$ from 0.1 to 75 μm.

6. The cosmetic composition of claim 1, wherein the surface-reacted calcium carbonate has a specific surface area of from 15 m$^2$/g to 200 m$^2$/g measured using nitrogen and the BET method.

7. The cosmetic composition of claim 1, wherein
the natural ground calcium carbonate is selected from the group consisting of marble, chalk, limestone, and mixtures thereof.

8. The cosmetic composition of claim 1, wherein the surface-reacted calcium carbonate is present in an amount from 0.1 to 50 wt.-%, based on the total weight of the cosmetic composition.

9. The cosmetic composition of claim 1, wherein the cosmetic composition further comprises at least one organic UV filter.

10. The cosmetic composition of claim 1, wherein the cosmetic composition further comprises at least one additive selected from the group consisting of bleaching agents, thickeners, stabilizers, chelating agents, preserving agents, wetting agents, emulsifiers, emollients, fragrances, colorants, skin tanning compounds, antioxidants, pigments, oils, water, and mixtures thereof.

11. The cosmetic composition of claim 1, wherein the cosmetic composition is a sunscreen product, an eye make-up product, a facial makeup product, a lip care product, a hair care product, a hair styling product, a nail care product, a hand care product, a skin care product, or a combination product thereof.

12. The cosmetic composition of claim 1, wherein the surface-reacted calcium carbonate is associated with at least one active agent selected from pharmaceutically active agents, biologically active agents, disinfecting agents, preservatives, flavouring agents, surfactants, oils, fragrances, essential oils.

* * * * *

UNITED STATES PATENT AND TRADEMARK OFFICE
CERTIFICATE OF CORRECTION

| | | |
|---|---|---|
| PATENT NO. | : 12,280,130 B2 | Page 1 of 1 |
| APPLICATION NO. | : 16/483909 | |
| DATED | : April 22, 2025 | |
| INVENTOR(S) | : Budde et al. | |

It is certified that error appears in the above-identified patent and that said Letters Patent is hereby corrected as shown below:

In the Claims

In Column 33, Line 25, in Claim 1, after "carbonate", insert --particles--

In Column 33, Line 28, in Claim 1, delete "cm$^{3/}$g," and insert --cm$^3$/g,-- therefor In Column 33, Line 30, in Claim 1, after "wherein", insert --:--

In Column 34, Line 42, in Claim 12, after "fragrances,", insert --and--

Signed and Sealed this
Second Day of December, 2025

John A. Squires
*Director of the United States Patent and Trademark Office*